(12) United States Patent
Ranganathan

(10) Patent No.: US 10,953,049 B2
(45) Date of Patent: Mar. 23, 2021

(54) METHODS FOR MAINTAINING AND IMPROVING KIDNEY FUNCTION IN PATIENTS WITH KIDNEY DISEASE AND ON STANDARD OF CARE THERAPY

(71) Applicant: KIBOW BIOTECH, INC., West Chester, PA (US)

(72) Inventor: Natarajan Ranganathan, Broomall, PA (US)

(73) Assignee: KIBOW BIOTECH INC., Newtown Square, PA (US)

( * ) Notice: Subject to any disclaimer, the term of this patent is extended or adjusted under 35 U.S.C. 154(b) by 0 days.

(21) Appl. No.: 16/619,145

(22) PCT Filed: Jun. 1, 2018

(86) PCT No.: PCT/US2018/035635
§ 371 (c)(1),
(2) Date: Dec. 4, 2019

(87) PCT Pub. No.: WO2019/005422
PCT Pub. Date: Jan. 3, 2019

(65) Prior Publication Data
US 2020/0138876 A1    May 7, 2020

Related U.S. Application Data

(60) Provisional application No. 62/591,442, filed on Nov. 28, 2017, provisional application No. 62/524,750, filed on Jun. 26, 2017.

(51) Int. Cl.
| | |
|---|---|
| *A61K 35/741* | (2015.01) |
| *A23L 33/26* | (2016.01) |
| *A23L 33/135* | (2016.01) |
| *A61P 13/12* | (2006.01) |

(52) U.S. Cl.
CPC .......... *A61K 35/741* (2013.01); *A23L 33/135* (2016.08); *A23L 33/26* (2016.08); *A61P 13/12* (2018.01); *A23V 2002/00* (2013.01); *A23Y 2220/03* (2013.01); *A23Y 2240/75* (2013.01); *A23Y 2300/55* (2013.01)

(58) Field of Classification Search
None
See application file for complete search history.

(56) References Cited

U.S. PATENT DOCUMENTS

| | | |
|---|---|---|
| 5,756,088 A | 5/1998 | Matsuura et al. |
| 6,706,263 B2 | 3/2004 | Ranganathan et al. |
| 6,706,287 B2 | 3/2004 | Ranganathan et al. |
| 7,993,903 B2 | 8/2011 | Hayakawa et al. |
| 7,998,470 B2 | 8/2011 | Ranganathan |
| 8,257,693 B2 | 9/2012 | Ranganathan |
| 8,481,025 B2 | 7/2013 | Ranganathan |
| 2005/0074442 A1 | 4/2005 | Ranganathan |
| 2009/0252709 A1 | 10/2009 | Nose et al. |

FOREIGN PATENT DOCUMENTS

WO    2007140622 A1    12/2007

OTHER PUBLICATIONS

Dylewski (Am J Kidney Dis (2013), vol. 61, No. 4:A1-A100, pp. A38).*
Ashlie, D. Amazon customer Review. Jun. 5, 2017, https://www.amazon.com/Renadyl-Formerly-Kibow-Biotics-Kidney/dp/B004G230Q4.
International Search Report and Written Opinion in PCT/US2018/035635 dated Aug. 29, 2018.
Ranganathan, N., P. Ranganathan, H. D'Silva, U. Vyas, B. Pechenyak & A. Weinberg (2017) "Quality of Life in Chronic Kidney Disease Patients Using a Synbiotic Dietary Supplement: A Survey." International Journal of Research Studies in Medical and Health Sciences 2(1):11-24.
Ranganathan, N., B. Pechenyak, U. Vyas, P. Ranganathan, A. Weinberg, P. Liang, M.C. Mallappallil, A.J. Norin, E.A. Friedman, S.J. Saggi (2014) "Randomized Controlled Trial of Strain-Specific Probiotic Formulation (Renadyl) in Dialysis Patients," BioMed Research International 2014:568571.
International Preliminary Report on Patentability issued in PCT/US2018/035635 dated Jan. 9, 2020.

* cited by examiner

*Primary Examiner* — Susan Hoffman
(74) *Attorney, Agent, or Firm* — Licata & Tyrrell P.C.

(57) ABSTRACT

Method for maintaining and improving reduced kidney function and improving quality of life in patients suffering from diseases that result in reduced renal function comprising administering RENDAYL™ in combination with standard of care treatment.

1 Claim, No Drawings

METHODS FOR MAINTAINING AND IMPROVING KIDNEY FUNCTION IN PATIENTS WITH KIDNEY DISEASE AND ON STANDARD OF CARE THERAPY

This application is a U.S. National Stage Application of PCT/US2018/035635 filed Jun. 1, 2018 and claims the benefit of priority to U.S. Provisional Application Ser. No. 62/524,750 filed Jun. 26, 2017 and 62/591,442 filed Nov. 28, 2017, the contents of each of which are incorporated herein by reference in their entirety.

BACKGROUND OF THE INVENTION

One of the main functions of the normal, healthy kidney, besides its regulatory, endocrine, and metabolic functions, is the disposal of waste products. Any impairment of excretory function can lead to the accumulation of a variety of nitrogenous waste products including, urea, creatinine and uric acid. High concentrations of waste products in the blood stream can exacerbate renal failure and promote kidney stones. Moreover, nitrogenous solutes in the circulating blood promote osmotic diffusion into the lumen because of the concentration gradient across the intestinal wall. This diffusion mechanism led to the concept of oral sorbents to augment gut-based clearance of nitrogenous waste products. Sorbents or microbes have demonstrated their ability to remove various compounds and nitrogenous wastes within the large bowel.

Urea-specific sorbents such as synthetic polymers and modified polysaccharides have been evaluated for the removal of urea and other nitrogenous wastes via the gut. Other sorbents such as oxidized starch, activated charcoal, and carob flour have also been investigated for the in vivo elimination of uremic toxins with some success. Prakash & Chang ((1996) *Nature Medicine* 2:883-88) demonstrated that microencapsulated, genetically-engineered *E. coli* DH5 are effective in removing urea and ammonia in an in vitro system. The same researchers obtained similar results in oral administration of *E. coli* DH5 cells in a uremic rat animal model. Bliss et al. ((1996) *Am. J. Clin. Nutr.* 63:392-398) have demonstrated that supplemental gum arabic fiber increases fecal nitrogen excretion and lowers urea nitrogen concentration in chronic renal failure patients consuming a low protein diet. Reinhart et al. ((1998) *Rec. Adv. In Canine and Feline Nutr. Iams Nutrition Symposium Proceedings.* Vol. II:395-404) found that canine renal patients fed a diet containing a fermentable fiber blend improved clinical end-stage renal disease status, suggesting that specific nutritional alteration allows repartitioning of nitrogen excretion away from the kidney and into the feces by colonic fermentation or additional bacterial growth.

U.S. Pat. No. 5,756,088 teaches a prescription diet for the prevention and treatment of dog and cat dermatosis comprising a composition containing a poly-unsaturated fatty acid such as γ-linolenic acid, γ-linolenic acid and docosahexaenoic acid, and/or biotin, and an antiflatulent such as a lactic acid bacterium, a *Bifidobacterium*, a *Lactobacillus*, a butyric acid bacterium or a *Bacillus*, and optionally an oligosaccharide.

U.S. Pat. No. 7,993,903 teaches a composition for inhibiting cholesterol absorption in the intestinal tract, wherein the composition includes *Bifidobacterium*, and optionally a *Lactobacillus* bacterium and carbohydrate.

US 2011/0171283 teaches a composition containing at least one nutrient, at least one disinfecting or decontaminating and/or at least one proteases inhibiting substance and/or complex of substances incorporated in an absorbent dressing for external care and/or treatment of wounds to a human or animal. In one embodiment, the protease inhibiting substance includes non-pathogenic acid producing micro-organisms (e.g., bifidobacteria, lactococci, or lactobacilli) and/or synbiotics (e.g., xylooligosaccharide).

US 2009/0252709 teaches a preventive or therapeutic agent for gastritis or ulcer, which includes as an active ingredient *Bifidobacterium bifidum*. This reference teaches that other microorganisms (e.g., *Bifidobacterium* or *Lactobacillus* bacteria), as well as sugars such as xylooligosaccharide.

WO 2007/140622 teaches a probiotic composition containing a mixture of a *Propionibacterium*, a *Lactobacillus*, a *Bifidobacterium* and a *Streptococcus*, wherein said composition can further include a prebiotic.

U.S. Pat. Nos. 6,706,263 and 6,706,287 disclose compositions and methods for alleviating symptoms of uremia comprising a mixture of sorbents and bacteria.

U.S. Pat. No. 7,998,470 teaches compositions and methods for improving renal function comprising a probiotic *Streptococcus* bacterium that is enterically coated.

U.S. Pat. No. 8,257,693 teaches compositions for improving renal function consisting of *L. acidophilus*, *B. longum*, and *S. thermophilus*.

U.S. Pat. No. 8,481,025 discloses compositions and methods for treating renal failure comprising *L. acidophilus*, *B. longum*, *S. thermophilus* and psyllium husks.

SUMMARY OF THE INVENTION

The present invention provides methods for maintaining and improving kidney function and improving quality of life in patients suffering from a disease that results in reduced kidney function comprising administering to a patient suffering from a disease that results in reduced kidney function an effective amount of a composition consisting of a RENADYL™ in combination with a standard of care treatment for the disease. RENADYL™ is a mixture of three probiotic bacteria (*S. thermophilus* strain KB 19, *L. acidophilus* strain KB 27, and *B. longum*) with two prebiotic components (xylooligosaccharide and inulin) in capsules containing 45 billion colony-forming units (CFUs). The method provides for maintenance or improvement of kidney function as well as improvement in the quality of life of the patients being treated. In certain embodiments, kidney function improvement includes at least a 2 mL/min increase in Glomerular Filtration Rate (GFR).

DETAILED DESCRIPTION OF THE INVENTION

Nitrogenous waste products accumulating in the blood stream have detrimental affects on health. Removal of nitrogenous wastes by diverting them into the colon, enteric dialysis, is a viable approach to decrease the negative impact that waste product accumulation has on an individual's physiology. The present invention is a method for maintaining or improving kidney function in patients suffering from different forms of kidney disease that involves administering to the patients a composition that combines the properties of probiotic and prebiotic components into a synbiotic product or composition to maintain or improve kidney function and improve quality of life in patients when combined with treatment regimens that are considered standard of care for the particular disease or condition being treated.

In the RENADYL™ composition used in this invention, the probiotic component is about 20% to about 70% of the total composition weight. In particular embodiments, the probiotic component is about 50% of the total composition weight. Likewise, the prebiotic component of the composition is about 20% to about 70% of the total composition weight or more preferably about 50% of the total composition weight.

The probiotic components of RENADYL™ consist of three different probiotic organisms: *S. thermophiles* strain KB 19, *L. acidophilus* strain KB 27, and *B. longum*. These three probiotic organisms have been shown to reduce nitrogenous wastes in blood of patients and to improve renal function (U.S. Pat. No. 8,257,693) and to be effective in the treatment of renal insufficiency (U.S. Pat. No. 8,481,025).

The prebiotic component of RENADYL™ is a non-digestive food that beneficially affects the host by selectively stimulating the growth and/or activity of one or more non-pathogenic bacteria in the colon and/or the growth and/or activity of one or more of the bacteria of the present composition. Prebiotic components are considered to have anti-carcinogenic, anti-microbial, hypolipidemic and glucose modulatory activities. They can also improve mineral absorption and balance. Furthermore, bacteria belonging to the *Bifidobacterium* and *Lactobacillus* families are stimulated by the presence of the prebiotic component and proliferate. Pharmacokinetically, prebiotic components reach the colon largely intact. Prebiotic components of RENADYL™ consist of inulin and xylooligosaccharide.

Xylooligosaccharide is included in RENADYL™ as it promotes the growth of *Bifidobacterium* and *Lactobacillus* bacteria. Similarly, inulin is included as it promotes the growth of *bifidobacteria* and also lowers the levels of p-cresol and p-cresyl sulphate in chronic kidney disease (CKD) patients (Salmean, et al. (2015) *J. Ren. Nutr.* 25(3): 316-320).

In the context of the present invention, "synbiotic" refers to a mixture of at least one probiotic component and at least one prebiotic component to promote health enhancing effects (Gibson and Roberfroid (1995) *J. Nutr.* 125:1401-1412). The ingestion of said synbiotic product reduces the blood concentration of nitrogenous waste products that accumulate in the circulating blood stream. In the case of RENADYL™, it has been observed that the composition composed of *S. thermophilus, L. acidophilus* and *B. longum* (45 billion total) can reduce urea levels by 60% in approximately 24 hours. These waste products can be of an endogenous origin such as normal or abnormal metabolic routes or bacterial putrefaction. Furthermore, the waste products can be of an exogenous origin as in dietary intake of proteins and amino acids. Furthermore, repeated ingestion of RENADYL™ itself has a highly beneficial effect upon the intestinal microflora by localization and colonization in the large intestine of microbes known to promote a healthy intestinal microenvironment.

Because the probiotic and prebiotic components of RENADYL™ are generally recognized as safe, they are consumed one, two or three times daily or more.

The present invention is a method for maintaining or improving kidney function and improving quality of life in a patient with reduced renal function, in particular in subjects with elevated levels of nitrogen-containing waste products. The method involves combining RENADYL™ treatment with the standard of care treatment that is already being administered to a patient. That standard of care will vary depending on the disease being treated. Administration of RENADYL™ has the additional beneficial effect of decreasing or reducing the levels of nitrogenous waste products in the blood to a normal range. For example, normal levels of creatinine in the blood are in the range of 0.6 to 1.2 mg/dL, whereas normal blood urea nitrogen (BUN) levels range from 7 to 18 mg/dL and normal uric acid levels in males and females is in the range of 2.1 to 8.5 mg/dL and 2.0 to 7.0 mg/dL, respectively. According, a subject with elevated creatinine, BUN and/or uric acid levels has levels that are above the normal range. Further, a BUN/creatinine ratio of 5 to 35 is indicative of normal levels of nitrogenous waste products in the blood. As one of skill in the art can appreciate, means for determining the levels of nitrogenous wastes are well-known to the skilled laboratory clinician.

Diseases contemplated for combination treatment with RENADYL™ and the standard of care include but would not be limited to those with diabetic nephropathy, hypertensive nephrosclerosis, glomerulonephritis, interstitial nephritis, or polycystic kidney disease wherein nephron function is impaired thereby decreasing glomerular filtration rate. One of skill in the art would understand what standard of care treatments would be combined based on the diagnosis made in a patient. For example, in a diabetic patient, a standard of care may be insulin or other drugs used to stabilize blood sugar levels that would include but not be limited to metformin, pioglitazone, rosiglitazone, glipizide, sitagliptin, and dapagliflozin. For other forms of kidney disease, many patients may be taking drugs such as anti-hypertensive agents, anti-inflammatory agents, and antibacterial agents, depending on the symptoms and causes of their disease. Standard of care may also include hemodialysis and peritoneal dialysis. RENADYL™ can be added to standard of care drug treatment regimens and provide beneficial effects on kidney function and quality of life, regardless of the standard of care treatment being used.

As a measure of kidney function, the method of the invention provides for an increase in GFR or a reduction in the GFR decline in the patient after treatment with RENADYL™ in combination with standard of care treatment as compared to before treatment with the combination therapy. In healthy adults, the average estimated GFR is more than 90. When GFR is below 60 for more than three months, a patient is typically diagnosed with moderate-to-severe chronic kidney disease. A GFR below 15 indicates kidney failure. Using the method of this invention, it was found that (1) GFR increased by at least 2 mL/min for an individual when the combination therapy was administered daily or (2) the decline in GFR observed in a patient with chronic kidney disease could be slowed or reduced by approximately 2-fold when the combination therapy was administered daily. Notably, the average increase in GFR for subjects receiving the combination treatment was at least 3.5 ml/min/1.73 m$^2$ per year, which corresponded to an approximate 10% improvement in GFR. When assessing quality of life, it was found that patients receiving treatment with RENADYL™ in combination with standard of care treatment experienced an increase in energy levels, increase in social interactions, increase in vigor, improved appetite, higher cognitive function, and/or ability to work continuously while receiving the combination treatment. Accordingly, the present method provides both a quantitative and qualitative improvement in patients with reduced renal function.

The invention is further described in the following examples, which does not limit the scope of the invention described in the claims.

Example 1: RENADYL™ in Combination with Standard of Care, a Case Study in Four Indian Patients Four patients had been taking RENADYL™ daily for the past nine months to four years. Patient 1 was a 77 year old man (67 kg) who had been on RENADYL™ for 10 months. Patient 2 was a 72 year old man (45 kg) who had been on RENADYL™ for four years. Patient 3 was a 55 year old man (71 kg) who had been on RENADYL™ for 9 months. Patient 4 was a 73 year old man (70 kg) who had been on RENADYL™ for one year. In addition to the standard care of therapy for their disease conditions, these patients had been taking two capsules of RENADYL™ (90 Billion CFUs) per day. The disease conditions included CKD (Patients 1, 2 and 4) and thin basement membrane glomerular nephropathy (Patient 3). Physical, mental, and laboratory parameters were measured during the patients' time taking RENADYL™. In addition, the patients evaluated their quality of life compared to their baseline condition (before they began taking RENADYL™).

During regularly scheduled visits, the physician would perform normal medical and physical exams. Progress or changes in respected health parameters were assessed during visits to the clinic. In addition to monitoring lab parameters, i.e., basic metabolic profile, CBC, and eGFR values, patients were asked to self-report changes in quality of life throughout the study. Adverse reactions to RENADYL™, drug-drug interactions, and other unusual incidents were evaluated.

Results were as follows. For Patient 1, GFR increased by 9 mL/min, while energy increased and allowed for increased exercising and social functioning. In Patient 2, GFR increased by 6 mL/min and the patient reported increased energy level. In Patient 3, GFR increased by 12 mL/min, and the patient reported to be actively working. In Patient 4, GFR increased by 6 mL/min and this patient also reported to be actively working.

In summary, all four CKD patients had comorbid conditions and adhered to all standard care of therapy for their conditions. Each patient tolerated the RENADYL™ treatment and reported no serious adverse effects. There was one report of flatulence which subsided. In addition, there were no drug-drug interactions reported between RENADYL™ and the medications prescribed for each individual. All individuals reported positive and improved quality of life. The documented improvement in GFR observed for all four patients confirmed RENADYL™'s ability to maintain healthy kidney function. Given the high expense of dialysis in India, the results are important in terms of the ability to improve patient outcomes.

Example 2: Survey of RENADYL™ Experience

Enteric dialysis through modulation of the gut microbiome to maintain healthy kidney function has proved to be helpful in many of those suffering from CKD. RENADYL™ has been available commercially since 2010 and during that time has been continually studied to assess efficacy. A short survey given to 600 RENADYL™ customers was distributed to ascertain how GFR changed, and the impact of use of RENADYL™ on quality of life after adding the dietary supplement to their standard of care therapy.

A written survey was distributed to customers asking the subject's age; gender; ethnicity; whether the subject was suffering from hypertension, heart disease, diabetes or other co-morbidities; when the subject began taking RENADYL™; what the subject's GFR was when they began taking RENADYL™; what the subject's present GFR was; whether RENADYL™ improved the subject's quality of life (less stress, more energy, greater productivity, higher activity level, better appetite, etc.). The survey also requested that the subject provide a brief and candid testimonial about their experience with RENADYL™ thus far. Similar surveys had been performed in 2013 and 2015, but in those surveys GFR data was not specifically requested as it was in the most recent survey described here.

Statistical analyses were performed on the GFR data to estimate RENADYL™'s impact on GFR, and quality of life. GFR was initially compared at two points in time, i.e., baseline and then at the time the survey was taken, via a paired student's t test. Since follow up time differed for each patient, average change in GFR per year was compared in a similar fashion. A mixed modeling procedure using PROC MIXED (SAS) was used to model GFR changes according to the various years of follow-up, and to discern whether there were differences in GFR over time. This procedure took into consideration the repeated measurements per patient and estimated whether GFR differed among the various years of follow-up. Since repeated measurements within patients may be correlated, this procedure allows one to model a "correlation structure", commonly referred to as a covariance pattern. Moreover, this estimate allowed for improved estimates of the standard errors of measurement. It also allowed for estimates at all-time points since data can be assumed to be missing at random (MAR).

There are a number of various covariance structures to choose from. Three of the more common covariance structures include compound symmetry (cs), for correlations that are constant for any two points in time, auto-regressive order one (ar1), for correlations that are smaller for time points further apart, and unstructured (un), which has no mathematical pattern within the covariance matrix. The compound symmetry (cs) structure provided the best fit. The potential role of other factors such as gender and/or hypertension in GRF changes over time also was examined using the mixed method procedure. Chi-square analysis was used to explore whether there was an association between gender and Quality of Life. Data were analyzed using SAS system software (SAS Institute Inc, Cary, N.C.).

Of the 600 surveys sent, 214 responses (35.6%) were received. In some cases, there was missing information in a response. For example, 206 (96.2%) stated the customers age, 196 (91.5% gave information about time of product ingestion, 150 (701%) answered questions on GFR before and after taking the supplement, and 200 (93.5%) volunteered information on gender (117 males and 83 females). The average age of the survey respondents was 69 years of age, with a range of 8 to 99 years of age. The average survey respondent has been using RENDYL™ for about 3 years. The GFR results are shown below in Table 1. The average GFR1 (baseline GFR) was 30.52 ml/min/1.73 $m^2$ (ranging from 4-100 mL/min/1.73 $m^2$), and the average GFR2 (most recent measured GFR) was 34.07 ml/min/1.73 $m^2$ (ranging from 5-106 mL/min/1.73 $m^2$). The average change in GFR from the beginning of RENADYL™ use to the respondents most recent doctors visit was an increase of 3.55 ml/min/1.73 $m^2$. The increase in GFR observed was statistically significant ($p<0.0013$). Of the surveys received, 140 contained complete information, including GFR. The lowest baseline GFR recorded was 4 ml/min, the highest was 100 ml/min (values consistent with end stage renal disease or ESRD to normal kidney function). The average baseline GFR of a survey participant was 30 ml/min (Stage IV CKD). The most recent GFR reported varied from 5 ml/min to 106 ml/min. The highest GFR impact was an increase of 65 ml/min, and the largest decrease in GFR was −40 ml/min. The average change in GFR for a survey participant was an increase of 2.90 ml/min.

TABLE 1

GFR Survey Data Results

| GFR Endpoint | Number of Patients | Mean (SD) |
| --- | --- | --- |
| GFR1 | 150 | 30.52 (17.24) |
| GFR2 | 150 | 34.07 (20.02) |
| Difference in GFR | 150 | 3.55 (13.24) |
| Year Change | 141 | 2.90 (8.40) |

Of the surveys sent, 200 of the survey respondents indicated a yes or no answer indicating whether or not RENADYL™ impacted their overall Quality of Life (Table 2). Results showed that 176 (88%) of respondents indicated RENADYL™ did in fact improve their overall quality of life, while only 12% of survey respondents indicated the product did not have an effect on overall quality of life. Data suggested that RENADYL™ may have been better at improving quality of life in women as compared to men, with 92% of women reporting that RENADYL™ improved overall quality of life, whereas only 84% of men reported improvement. This result was not found to be statistically significant (p<0.08)

TABLE 2

RENADYL ™'s Impact on Quality of Life

| Quality of Life | Gender | | |
| --- | --- | --- | --- |
| Frequency Percent (%) | Female | Male | Total |
| Number Answering "No" | 6 | 18 | 24 |
| % of Male/Female | 3 | 9 | 12 |
| % Number by Male/Female | 7.23 | 15.38 | |
| Number Answering "Yes" | 77 | 99 | 176 |
| % of Male/Female | 38.5 | 49.5 | 88 |
| % Number by Male/Female | 92.77 | 84.62 | |
| Total Number Responding | 83 | 117 | 200 |
| % Male/Female | 41.5 | 58.5 | 100 |

The FDA and National Kidney Foundation guideline for determining effectiveness of primary endpoints in CKD treatments/therapies is reduction in the decline of GFR by 30% (40% is preferred). The results of the RENADYL™ survey suggest that these guidelines would be exceeded in a large-scale, double-blind, placebo controlled trial. The survey results showed that RENADYL™ had a positive impact on kidney function. On average, a 3.5 mL/min/1.73 m$^2$ increase in GFR would translate to an 11.6% improvement in GFR (the average GFR at the start of taking RENADYL™ was 30 mL/min/1.73 m$^2$). With such strong improvements in GFR, it is not surprising to see that 88% of survey respondents indicated that their quality of life improved after taking RENADYL™. Two prior customer surveys were distributed in 2013 and 2015 that focused on ascertaining quality of life information. In the 2013 survey, 72% of respondents indicated that RENADYL™ improved quality of life, while in the 2015 survey, 73% of respondents indicated improvements in quality of life. In the current survey, similar improvements were reported by patients.

Another way to describe the results obtained in this survey, is to compare the impact of RENADYL™ use to normal CKD progression, as well as theoretical results that could be obtained using any interventional therapy that decreases the progression of CKD by 40%, which is the preferred National Kidney Foundation (NKF)/FDA guideline primary endpoint. Table 3 demonstrates the possible impact of RENADYL™ using these comparisons. A period of 3 years was applied to coincide with the NKD/FDA guideline. The average survey respondent had a baseline GFR close to 30 ml/min/1.73 m$^2$, therefore, this value was used as a baseline. The average increase for responders was 3.5 ml/min/1.73 m$^2$, dividing that by the average time of three years they took the product gives an average per year increase in GFR of 2.9 ml/min. The normal progression of CKD based on the 2017 study conducted by Tsai et al. (PLoS ONE 12) would lead to a decrease in GFR of 4.42 ml/min/1.73 m$^2$ per year. Using this as the normal progression, the NKF/FDA preferred guideline would reduce decline in GFR by 40%. Thus, the annual decrease in GFR would be 2.6 ml/min per year. After a baseline (year 1) and two follow-up years, the GFR of a CKD person using the product would be 32.4 ml/min, a person with normal progression would be at 21.2 ml/min, and a person using a therapy resulting in 40% slower progression would be 24.8 ml/min. Thus, a RENADYL™ user would have a GFR that was 11.2 ml/min better than someone who is experiencing normal progression of CKD, and a RENADYL™ user would have a GFR that was 7.8 ml/min better than someone using a theoretical therapy that met the 40% guideline.

TABLE 3

RENADYL ™ Compared to Normal Progression and Preferred NKF/FDA Endpoint

| Year | Product GFR (ml/min/1.73 m$^2$) | Average Progression of CKD (ml/min/1.73 m$^2$) | NKF/FDA Preferred Endpoint (40% Progression) (ml/min/1.73 m$^2$) |
| --- | --- | --- | --- |
| 1 (baseline) | 30 | 30 | 30 |
| 2 | 32.9 | 25.6 | 27.4 |
| 3 | 35.8 | 21.2 | 24.8 |

Notes:
Estimated progression of CKD for 3 years based on RENADYL ™ survey results.

Considered together, the survey data showed that RENADYL™ had beneficial effects to improve GFR and improve Quality of Life in patients with CKD. Future controlled clinical studies are planned to further investigate the effects of RENADYL™.

Example 3: Long-Term RENADYL™ Use in a Patient with Juvenile Diabetes and Nephropathy Individual patient experience reports also provide important information supporting the efficacy of RENADYL™ in humans. RENADYL™ use in a male patient for 11 years has been reported. The patient had been diagnosed with juvenile diabetic nephropathy. Beginning Jun. 17, 2006, the patient began treatment with RENADYL™. The dosage was 90 billion CFUs per day for the 11 year period. The individual was diagnosed with Juvenile diabetes in 1961 (56 years ago), and nephropathy was diagnosed in 1986. The patient is currently taking nine prescription medications and insulin (insulin pump) for other health issues, and diabetes (Type I) respectively. The patient reported his lab parameters and quality of life throughout the 11 year study.

The patient's GFR fluctuated from 41.7 to 24 mL/min/ 1.73 m², during the 11 years of the case study. On average, the patient's GFR declined by 1.6 mL per year. The patient always reported improved quality of life such as: more vigor, improved appetite, higher cognitive function, and ability to work continuously throughout the 11 year study period. No drug-drug interactions were reported during this long-term study.

On average, the GFR of a person suffering from diabetic nephropathy decreases roughly 3.3 mL per year (Alwakeel et al. (2011) *Ann. Saudi Med.* 31:236-42). As presented in Table 4, this individual's GFR decreased by 1.6 mL per year. These results indicate that RENADYL™ reduced the decline in GFR per year by a factor of two. The dietary supplement also helped improve overall quality of life, allowing the patient to continue his normal life.

TABLE 4

GFR Analysis

| Date | BUN[1] | Creat-inine[2] | GFR[3] | K[4] | Glucose[5] | Uric Acid[6] |
|---|---|---|---|---|---|---|
| Feb. 9, 2017 | 66 | 2.66 | 24 | 5.2 | 190 | 9.4 |
| Oct. 27, 2016 | 49 | 2.53 | 25 | 4.7 | 199 | 8.5 |
| Oct. 5, 2016 | 66 | 3.08 | 20 | 4.6 | 101 | 9.9 |
| Jul. 25, 2015 | 50 | 2.47 | 26 | 4.7 | 192 | 11.5 |
| Mar. 10, 2015 | 62 | 2.47 | 26 | 4.9 | 147 | |
| May 5, 2014 | 41 | 2.19 | 31 | 5.2 | 157 | 7.2 |
| Sep. 3, 2013 | 38 | 2.1 | 32 | 4.5 | 160 | 7.3 |
| Jun. 28, 2013 | 31 | 1.86 | 37 | 5.4 | 141 | 5.8 |
| Apr. 24, 2013 | 36 | 1.91 | 36 | 5.6 | 149 | 6.7 |
| Apr. 8, 2013 | 72 | 2.6 | 25 | 5.6 | 115 | 7.5 |
| Feb. 8, 2013 | 62 | 2.57 | 25 | 4.8 | 127 | |
| Aug. 30, 2012 | 44 | 2.3 | 29 | 5.1 | 143 | 8.8 |
| Aug. 8, 2012 | 34 | 2.2 | 30 | 4.4 | 87 | |
| Nov. 10, 2011 | 43 | 1.81 | 37 | 5.1 | 195 | 6.5 |
| Jul. 8, 2011 | 46 | 2.1 | 32 | 5.1 | 103 | 7.6 |
| Aug. 23, 2010 | 49 | 2.1 | 32 | 5.2 | 180 | 8 |
| Mar. 23, 2010 | 43 | 1.81 | 39 | 5.1 | 195 | 6.5 |
| Dec. 22, 2009 | 46 | 2.1 | 32 | 5.1 | 103 | 7.6 |
| Nov. 15, 2009 | 61 | 1.9 | 39.2 | 5.4 | 166 | 9.5 |
| Oct. 7, 2009 | 43 | 1.94 | 36 | 5.7 | 192 | 7.6 |
| May 15, 2009 | 59 | 2.1 | 33 | 4.9 | 94 | 8 |
| Feb. 3, 2009 | 41 | 1.8 | 41.4 | 5.1 | 185 | 6.9 |
| Oct. 20, 2008 | 47 | 2.3 | 31.2 | 5.5 | 196 | |
| Aug. 18, 2008 | 31H | 2.23H | 30L | 5.1 | 150H | |
| Jun. 18, 2008 | 39H | 1.82H | 39L | 4.8 | 62L | 8.2H |
| Mar. 10, 2008 | 55H | 2.05H | 34L | 5.1 | 156H | |
| Dec. 31, 2007 | 50 | 1.9 | 39 | 5.4 | 156 | 8.3 |
| Sep. 24, 2007 | 49H | 1.9H | 39L | 5.3 | 154H | 8.3H |
| May 14, 2007 | 45 | 1.9 | 39.2 | 5.6 | 194 | 8.6 |
| Apr. 5, 2007 | 41 | 1.9 | 36.9 | 4.7 | 126 | |
| Mar. 8, 2007 | 55 | 2.1 | 34.9 | 5.6 | 210 | 9.8 |
| Nov. 13, 2006 | | | | | | 9.5 |
| Oct. 16, 2006 | 50 | 2 | 36.9 | 4.9 | 143 | 8.6 |
| Sep. 14, 2006 | 40 | 2 | 36.9 | 5.3 | 67 | |
| Aug. 28, 2006 | 44 | 1.8 | 41.8 | 5.6 | 169 | 8.7 |
| Jul. 17, 2006 | 39 | 1.8 | 41.7 | 5.4 | 110 | |

[1]Blood urea nitrogen (mg/dL), ~9-23 mg/dL is considered normal.
[2]Creatinine (mg/dL), ~0.0-1.3 mg/dL is considered normal.
[3]Glomular filtration rate (mL/min/1.73 m²), >60 mL/min/1.73 m² is considered normal.
[4]Potassium (MEQ/L), 3.5-5.1 MEQ/L is considered normal.
[5]Glucose (mg/dL), 70-105 mg/dL is considered normal.
[6]Uric acid (mg/dL), 3.5-7 mg/dL is considered normal.

Example 4: Combining RENADYL™ with Standard Care of Therapy in Predialysis and Dialysis Patients Probiotics and prebiotics are widely used for digestive and immune health. RENADYL™ is a dietary supplement consisting of both prebiotic and probiotic components that has demonstrated its potential to reduce serum uremic toxins. Outcomes and data from various published papers on use of pro/prebiotics and RENADYL™ for kidney failure patients including three customer surveys were analyzed. Three pilot scale clinical trials and three biennial surveys (2013, 2015, 2017) of customers taking RENADYL™ showed that the strains in RENADYL™ benefit the renal failure population by several distinct mechanisms. These include 1) removal of nitrogenous wastes by *S. thermophilus*. The organism metabolizes uremic toxins, i.e., urea, uric acid and creatinine, resulting in increased growth of beneficial bacteria and reduction in growth of pathogens; 2) all three probiotic RENADYL™ strains produce bacteriocins (antimicrobial molecules), which further inhibit the growth of pathogens; 3) *L. acidophilus* reduces levels of cardiovascular toxins TMA and TMAO; 4) *B. longum* reduces production of phenols, cresols and other toxins, which get bound to serum proteins and cannot be removed by routine dialysis; and 5) modulation of inflammation, where inflammatory biomarkers like C-reactive protein (CRP) decreased.

The analysis demonstrated that enteric dialysis with RENADYL™ was safe and well-tolerated. It is non-invasive and less expensive. Hemo/Peritoneal dialysis is unable to reduce protein bound uremic toxins like indoles, cresols and other middle molecules. These toxins are associated with poor quality of life. Imbalanced gut microflora leads to high levels of uremic toxins, protein bound toxins, and infections such as Hepatitis C. RENADYL™ removes these toxins, lowers chronic inflammation, and stabilizes the gut microbiome thus providing benefit to pre-dialysis and dialysis patients regardless of age, sex, ethnicity, and comorbid conditions. RENADYL™ also appeared to have a stabilizing effect on overall health status and improved quality of life in the patient populations.

What is claimed is:

1. A method for maintaining or improving kidney function and improving quality of life in a patient with reduced renal function comprising
   (a) administering to a patient suffering from a disease that results in reduced renal function an effective amount of a composition comprising xylooligosaccharide, inulin and 45 billion colony-forming units of probiotic bacteria consisting of *Streptococcus thermophilus*, *Lactobacillus acidophilus*, and *Bifidobacterium longum*, in combination with
   (b) standard of care treatment selected from the group consisting of insulin, metformin, pioglitazone, rosiglitazone, glipizide, sitagliptin, dapagliflozin, an anti-hypertensive agent, an anti-inflammatory agent, an antibacterial agent, hemodialysis, peritoneal dialysis or a combination thereof;
   thereby maintaining or improving kidney function and improving quality of life in the patient, wherein kidney function improvement comprises at least a 2 mL/min increase in glomerular filtration rate and quality of life improvement is selected from the group consisting of increased energy level, increased social interactions, increased vigor, improved appetite, improved cognitive function, improved ability to work, or a combination thereof.

* * * * *